(12) United States Patent
Calloway et al.

(10) Patent No.: US 12,318,150 B2
(45) Date of Patent: Jun. 3, 2025

(54) CAMERA TRACKING SYSTEM FOR COMPUTER ASSISTED SURGERY NAVIGATION

(71) Applicant: GLOBUS MEDICAL, INC., Audubon, PA (US)

(72) Inventors: Thomas Calloway, Pelham, NH (US); Sanjay Joshi, Andover, MA (US); Tushar Sawant, Newton, MA (US); Rand Kmiec, Nashua, NH (US); Norbert Johnson, North Andover, MA (US)

(73) Assignee: Globus Medical Inc., Audubon, PA (US)

( * ) Notice: Subject to any disclaimer, the term of this patent is extended or adjusted under 35 U.S.C. 154(b) by 232 days.

(21) Appl. No.: 18/045,474

(22) Filed: Oct. 11, 2022

(65) Prior Publication Data

US 2024/0115325 A1    Apr. 11, 2024

(51) Int. Cl.
*A61B 34/20* (2016.01)
*A61B 90/00* (2016.01)
*G06T 7/80* (2017.01)

(52) U.S. Cl.
CPC .......... *A61B 34/20* (2016.02); *A61B 90/361* (2016.02); *G06T 7/85* (2017.01);
(Continued)

(58) Field of Classification Search
None
See application file for complete search history.

(56) References Cited

U.S. PATENT DOCUMENTS

| 4,150,293 A | 4/1979 | Franke |
| 5,246,010 A | 9/1993 | Gazzara et al. |

(Continued)

FOREIGN PATENT DOCUMENTS

| EP | 3942523 A1 | 1/2022 |
| JP | 2021194544 A | 12/2021 |

(Continued)

OTHER PUBLICATIONS

US 8,231,638 B2, 07/2012, Swarup et al. (withdrawn)
(Continued)

*Primary Examiner* — Christopher Braniff

(57) ABSTRACT

A camera tracking system for computer assisted navigation during surgery. Operations identify locations of markers of a reference array in images obtained from tracking cameras imaging a real device. Operations determine measured coordinate locations of a feature of a real device in the images based on the identified locations of the markers and based on a relative location relationship between the markers and the feature. Operations process a region of interest in the images identified based on the measured coordinate locations through a neural network configured to output a prediction of coordinate locations of the feature in the images. The neural network has been trained based on training images containing the feature of a computer model rendered at known coordinate locations. Operations track pose of the feature of the real device in 3D space based on the prediction of coordinate locations of the feature of the real device in the images.

6 Claims, 14 Drawing Sheets

(52) U.S. Cl.
CPC ............... *A61B 2034/2055* (2016.02); *A61B 2090/3937* (2016.02); *A61B 2090/3983* (2016.02); *G06T 2207/10028* (2013.01); *G06T 2207/20081* (2013.01); *G06T 2207/30004* (2013.01); *G06T 2207/30204* (2013.01); *G06T 2207/30244* (2013.01)

(56) References Cited

U.S. PATENT DOCUMENTS

| | | | |
|---|---|---|---|
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,012,216 | A | 1/2000 | Esteves et al. |
| 6,031,888 | A | 2/2000 | Van et al. |
| 6,033,415 | A | 3/2000 | Mittelstadt et al. |
| 6,080,181 | A | 6/2000 | Jensen et al. |
| 6,106,511 | A | 8/2000 | Jensen |
| 6,122,541 | A | 9/2000 | Cosman et al. |
| 6,144,875 | A | 11/2000 | Schweikard et al. |
| 6,157,853 | A | 12/2000 | Blume et al. |
| 6,167,145 | A | 12/2000 | Foley et al. |
| 6,167,292 | A | 12/2000 | Badano et al. |
| 6,201,984 | B1 | 3/2001 | Funda et al. |
| 6,203,196 | B1 | 3/2001 | Meyer et al. |
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,306,126 | B1 | 10/2001 | Montezuma |
| 6,312,435 | B1 | 11/2001 | Wallace et al. |
| 6,314,311 | B1 | 11/2001 | Williams et al. |
| 6,320,929 | B1 | 11/2001 | Von Der Haar |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,501,981 | B1 | 12/2002 | Schweikard et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,636,757 | B1 | 10/2003 | Jascob et al. |
| 6,645,196 | B1 | 11/2003 | Nixon et al. |
| 6,666,579 | B2 | 12/2003 | Jensen |
| 6,669,635 | B2 | 12/2003 | Kessman et al. |
| 6,701,173 | B2 | 3/2004 | Nowinski et al. |
| 6,757,068 | B2 | 6/2004 | Foxlin |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,922,632 | B2 | 7/2005 | Foxlin |
| 6,968,224 | B2 | 11/2005 | Kessman et al. |
| 6,978,166 | B2 | 12/2005 | Foley et al. |
| 6,988,009 | B2 | 1/2006 | Grimm et al. |
| 6,991,627 | B2 | 1/2006 | Madhani et al. |
| 6,996,487 | B2 | 2/2006 | Jutras et al. |
| 6,999,852 | B2 | 2/2006 | Green |
| 7,007,699 | B2 | 3/2006 | Martinelli et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |
| 7,366,562 | B2 | 4/2008 | Dukesherer et al. |
| 7,379,790 | B2 | 5/2008 | Toth et al. |
| 7,386,365 | B2 | 6/2008 | Nixon |
| 7,422,592 | B2 | 9/2008 | Morley et al. |
| 7,435,216 | B2 | 10/2008 | Kwon et al. |
| 7,440,793 | B2 | 10/2008 | Chauhan et al. |
| 7,460,637 | B2 | 12/2008 | Clinthorne et al. |
| 7,466,303 | B2 | 12/2008 | Yi et al. |
| 7,493,153 | B2 | 2/2009 | Ahmed et al. |
| 7,505,617 | B2 | 3/2009 | Fu et al. |
| 7,533,892 | B2 | 5/2009 | Schena et al. |
| 7,542,791 | B2 | 6/2009 | Mire et al. |
| 7,555,331 | B2 | 6/2009 | Viswanathan |
| 7,567,834 | B2 | 7/2009 | Clayton et al. |
| 7,594,912 | B2 | 9/2009 | Cooper et al. |
| 7,606,613 | B2 | 10/2009 | Simon et al. |
| 7,607,440 | B2 | 10/2009 | Coste-Maniere et al. |
| 7,623,902 | B2 | 11/2009 | Pacheco |
| 7,630,752 | B2 | 12/2009 | Viswanathan |
| 7,630,753 | B2 | 12/2009 | Simon et al. |
| 7,643,862 | B2 | 1/2010 | Schoenefeld |
| 7,660,623 | B2 | 2/2010 | Hunter et al. |
| 7,661,881 | B2 | 2/2010 | Gregerson et al. |
| 7,683,331 | B2 | 3/2010 | Chang |
| 7,683,332 | B2 | 3/2010 | Chang |
| 7,689,320 | B2 | 3/2010 | Prisco et al. |

(56) References Cited

U.S. PATENT DOCUMENTS

| | | |
|---|---|---|
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Voll et al. |

(56) References Cited

U.S. PATENT DOCUMENTS

| | | |
|---|---|---|
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |

(56) References Cited

U.S. PATENT DOCUMENTS

| | | |
|---|---|---|
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Avallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |

(56) References Cited

U.S. PATENT DOCUMENTS

| | | |
|---|---|---|
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2020/0297425 A1 | 9/2020 | Helm et al. |
| 2020/0305984 A1* | 10/2020 | Zhao .................... A61B 34/20 382/128 |
| 2021/0391058 A1 | 12/2021 | Kostrzewski et al. |
| 2022/0061921 A1 | 3/2022 | Crawford et al. |
| 2024/0185432 A1* | 6/2024 | Polchin ................ G06V 10/772 |

FOREIGN PATENT DOCUMENTS

| | | |
|---|---|---|
| WO | 2020190884 A1 | 9/2020 |
| WO | 2021134132 A1 | 7/2021 |

OTHER PUBLICATIONS

Crawford Neil et al: "Ensuring navigation integrity using robotics in spine surgery", Journal of Robotic Surgery, Springer London, London, vol. 14, No. 1, Apr. 15, 2019 (Apr. 15, 2019), pp. 177-183.

* cited by examiner

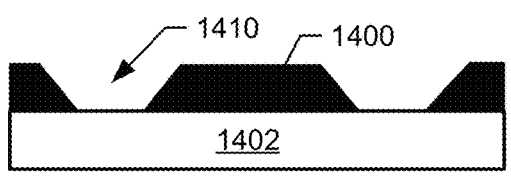
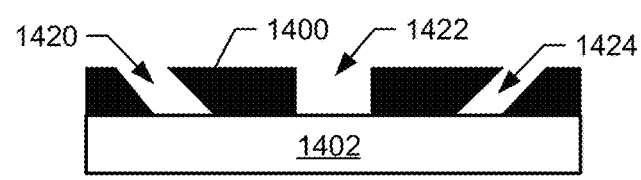
Fig. 14a　　　　　　Fig. 14b
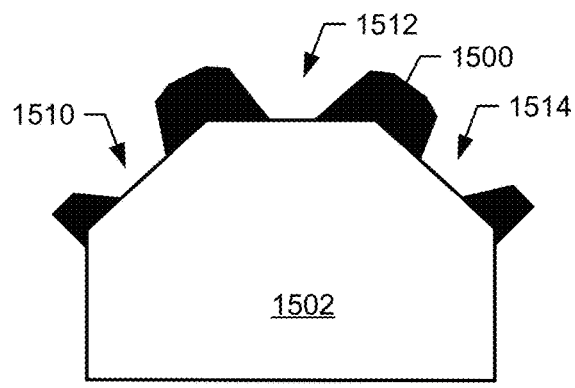
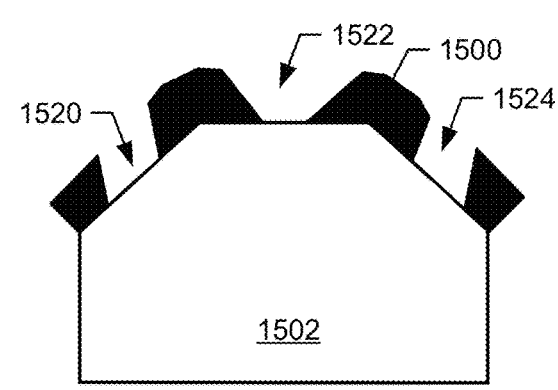
Fig. 15a　　　　　　Fig. 15b

CAMERA TRACKING SYSTEM FOR COMPUTER ASSISTED SURGERY NAVIGATION

FIELD

The present disclosure relates to medical devices and systems, and more particularly, camera tracking systems used for computer assisted navigation during surgery.

BACKGROUND

A computer assisted surgery navigation system has become a well-established technique in an operating room for provide a surgeon with computerized visualization of how a surgical instrument or other device that is posed relative to a patient correlates to a pose relative to medical images of the patient's anatomy, and how those poses correlate to a pre-operative surgical plan. Camera tracking systems for computer assisted surgery navigation typically use a set of tracking cameras to track pose of a reference array on the surgical instrument, which is being positioned by a surgeon during surgery, relative to a patient reference array (also "dynamic reference base" (DRB)) affixed to a patient. A computer model of a real instrument is associated with a reference element, so that the computer model can be overlaid on registered images of patient's anatomy. The camera tracking system uses the relative poses of the reference arrays to determine how the real instrument is posed relative to a patient and to determine how the computer model of the real instrument is to be correspondingly posed as on overlay on the medical images. The surgeon can thereby use real-time visual feedback of the relative poses to navigate the surgical instrument during a surgical procedure on the patient.

To ensure fidelity of the instrument computer model overlaid on the medical images, accuracy of the real instrument relative to the computer model needs to be verified prior to use. The accuracy check can be performed by bringing the tip of the tracked real instrument into a divot associated with another reference element. The divot is typically a cone-shaped depression. FIG. 5 illustrates an instrument that can be tracked by the camera tracking system as its tip is touched to a verification divot on an arm supporting a tracked reference array which is also tracked by the camera tracking system. The predicted position of the instrument tip determined based on the instrument computer model is compared with the measured position determined based on the tracked position of the divot. Assuming the user has properly positioned the instrument tip in the divot, the distance between the predicted and measured positions determines the accuracy of the tracked instrument. If the accuracy check does not pass, that instrument is not verified and should not be used.

Example Sources of Inaccuracies During Instrument Verification Include:
1. Deformed instrument, e.g., bent tip;
2. Deformed reference element, e.g., bent reference array fixture or bent marker mounting post, where it is noted that a relatively small angular shift in the reference element can result in corresponding very small error for tracking of the reference element, but result in a much larger error for tracking the instrument tip; and
3. Inaccuracies in optical markers due to manufacturing defects, smudges, or inaccurate mounting of optical markers on mounting posts or within marker mounting sockets.

Verification of the instrument at time of use can enable compensative for inaccuracies and improve the fidelity of tracking so that the measured location of the physical tip matches the model-based prediction.

SUMMARY

Some embodiments of the present disclosure are directed to a camera tracking system for computer assisted navigation during surgery. The system includes at least one processor configured to perform operations that include to identify locations of markers of a reference array in a set of the images obtained from tracking cameras imaging a real device with at least partially overlapping field-of-views. The operations determine measured coordinate locations of a feature of a real device in the set of the images based on the identified locations of the markers and based on a relative location relationship between the markers and the feature. The operations process a region of interest in the set of the images identified based on the measured coordinate locations through a neural network configured to output a prediction of coordinate locations of the feature in the set of the images. The neural network has been trained based on training images containing the feature of a computer model rendered at known coordinate locations. The operations track pose of the feature of the real device in three-dimensional (3D) space based on the prediction of coordinate locations of the feature of the real device in the set of the images.

Some other embodiments of the present disclosure are directed to another camera tracking system for computer assisted navigation during surgery. The system includes at least one processor configured to perform operations that include to obtain images from accuracy cameras imaging a calibration pattern with at least partially overlapping field-of-views, wherein the accuracy cameras are connected to a reference array of markers through a rigid fixture. The operations identify an actual calibration pattern in the images from the accuracy cameras. The operations compute an expected calibration pattern in the images from the accuracy cameras based on a relative pose of the accuracy cameras. The operations adjust the relative pose of the accuracy cameras based on difference between the actual calibration pattern and the expected calibration pattern in the images from the accuracy cameras.

Some other embodiments of the present disclosure are directed to another camera tracking system for computer assisted navigation during surgery. The system includes at least one processor configured to perform operations that include to identify coordinates of a pattern of spaced-apart light reflective material areas along a continuous surface of a reference marker attached to a real device in images obtained from tracking cameras imaging the reference marker with at least partially overlapping field-of-views. The operations track pose of the reference marker in 3D space based on the identified coordinates of the pattern of spaced-apart light reflective material areas along the continuous surface of the reference marker.

Some other embodiments of the present disclosure are directed to a reference marker configured to be tracked by a camera tracking system for computer assisted navigation during surgery. The reference marker includes an object with a surface of one of a light absorptive material and a light reflective material, and a cover layer extending across the surface of the object. The cover layer is the other one of the light absorptive material and the light reflective material.

The cover layer has a pattern of openings exposing spaced-apart areas of the surface of the object.

Other camera tracking systems and reference markers according to embodiments of the inventive subject matter will be or become apparent to one with skill in the art upon review of the following drawings and detailed description. It is intended that all such additional camera tracking systems and reference markers be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings:

FIGS. 13, 14a, 14b, 15a, 15b, and 16 illustrate a portion of different embodiments of reference markers having a cover layer with a pattern of openings exposing spaced-apart areas of an underlying object surface for tracking by a camera tracking system.

DETAILED DESCRIPTION

Figure 1:
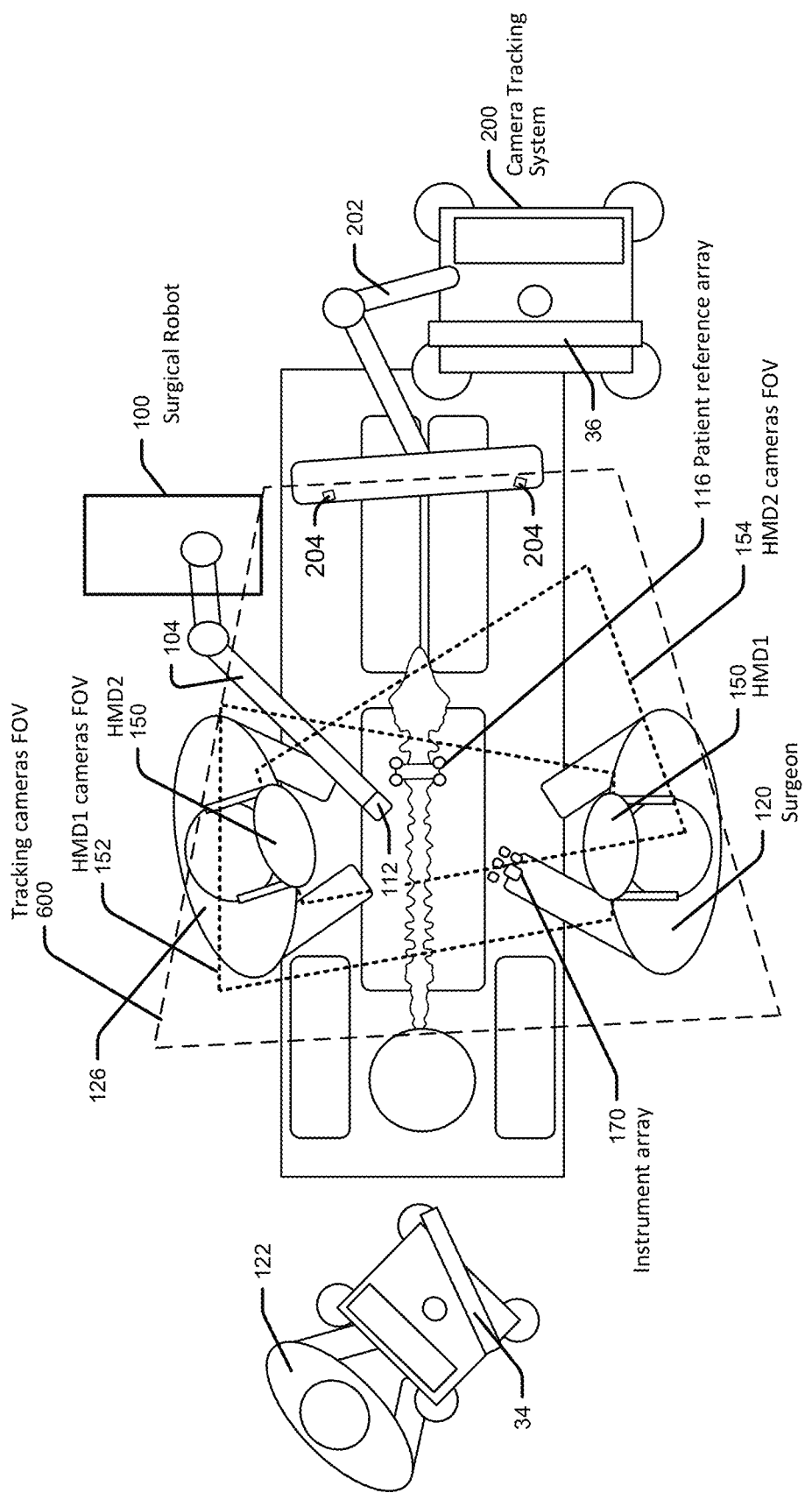
FIG. 1 is an overhead view of a surgical system arranged during a surgical procedure in a surgical room which includes a camera tracking system for navigated surgery and which may further include a surgical robot for robotic assistance according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "attached", "supported," and "coupled" and variations thereof are used broadly and encompass both direct and indirect mountings, connections, attachments, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Some embodiments of the present disclosure are directed to various camera tracking systems for verifying instruments and other devices at time of use and tracking pose of the instruments and other devices during computer assisted navigation during surgery. Some other embodiments are directed to reference markers which are configured to be tracked by a camera tracking system for computer assisted navigation during surgery. Before describing these embodiments is detail, various components that may be used for performing embodiments in a navigated surgery system are described with reference to FIGS. 1-4.

Figure 2:
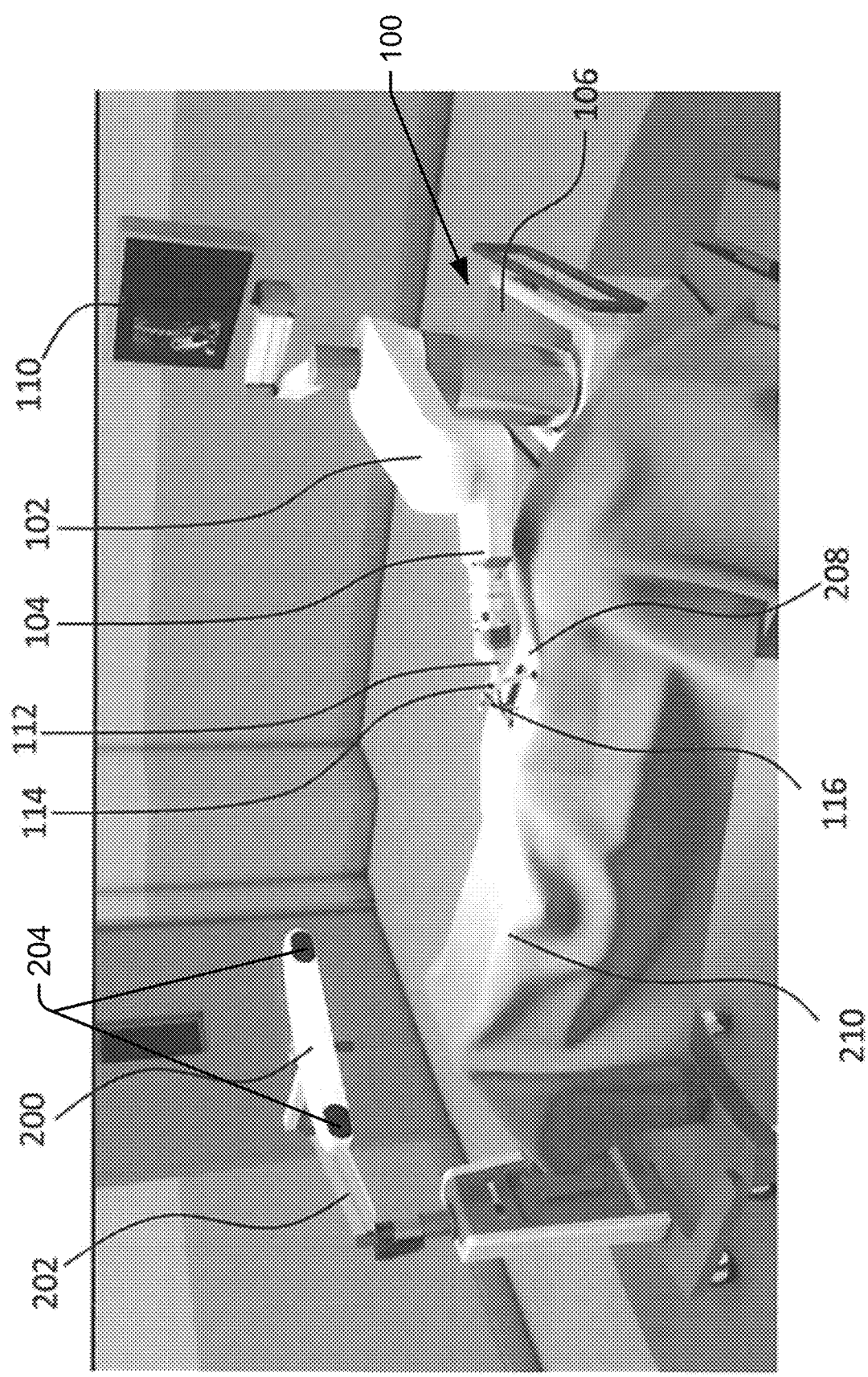
FIG. 2 illustrates the camera tracking system and the surgical robot positioned relative to a patient according to some embodiments.
Figure 3:
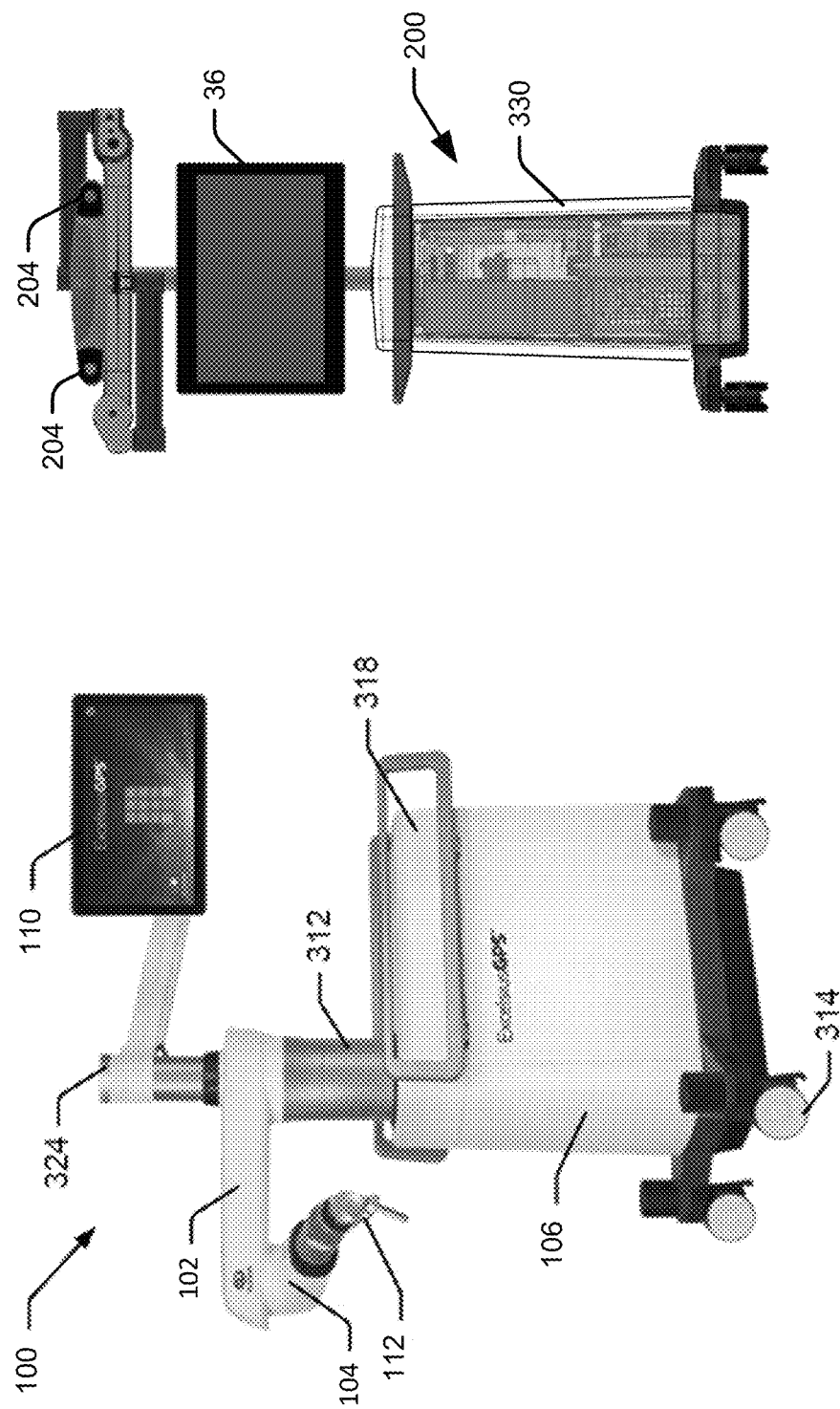
FIG. 3 further illustrates the camera tracking system and the surgical robot configured according to some embodiments.
Figure 4:
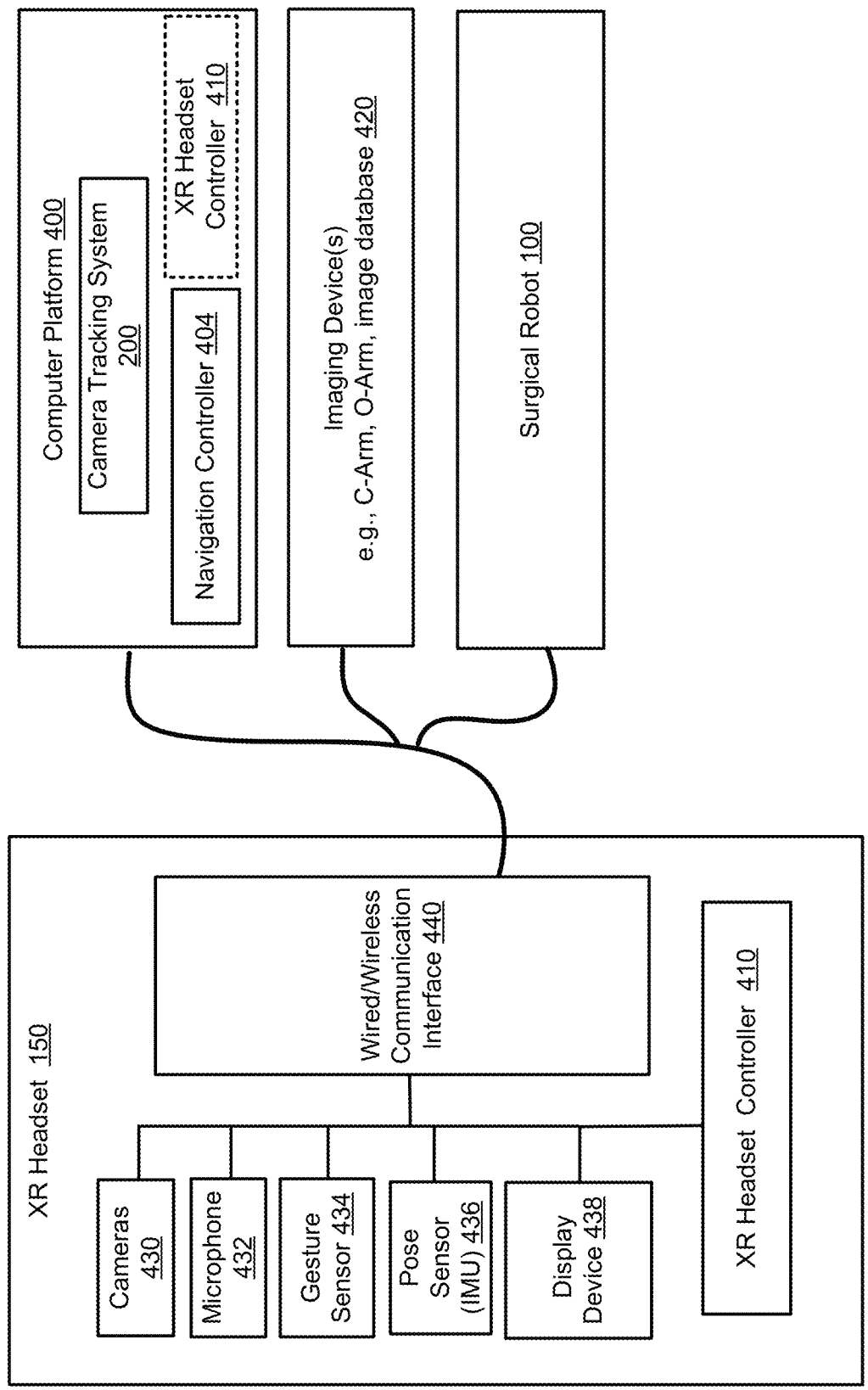
FIG. 4 illustrates a block diagram of a surgical system that includes an XR headset, a computer platform, imaging devices, and a surgical robot which are configured to operate according to some embodiments.

FIG. 1 is an overhead view of a surgical system arranged during a surgical procedure in a surgical room which includes a camera tracking system 200 for navigated surgery and which may further include a surgical robot 100 for robotic assistance according to some embodiments. FIG. 2 illustrates the camera tracking system 200 and the surgical robot 100 positioned relative to a patient according to some embodiments. FIG. 3 further illustrates the camera tracking system 200 and the surgical robot 100 configured according to some embodiments. FIG. 4 illustrates a block diagram of a surgical system that includes an XR headset 150, a computer platform 400, imaging devices 420, and the surgical robot 100 which are configured to operate according to some embodiments.

The XR headsets 150 may be configured to augment a real-world scene with computer generated XR images while worn by personnel in the operating room. The XR headsets 150 may be configured to provide an augmented reality (AR) viewing environment by displaying the computer generated XR images on a see-through display screen that allows light from the real-world scene to pass therethrough for combined viewing by the user. Alternatively, the XR headsets 150 may be configured to provide a virtual reality (VR) viewing environment by preventing or substantially preventing light from the real-world scene from being directly viewed by the user while the user is viewing the computer-generated AR images on a display screen. The XR headsets 150 can be configured to provide both AR and VR viewing environments. Thus, the term XR headset can referred to as an AR headset or a VR headset.

Referring to FIGS. 1-4, the surgical robot 100 may include, for example, one or more robot arms 104, a display 110, an end-effector 112, for example, including a guide tube 114, and an end effector reference array which can include one or more tracking markers. A patient reference array 116 (DRB) has a plurality of tracking markers 117 and is secured directly to the patient 210 (e.g., to a bone of the patient 210). A reference array 170 is attached or formed on an instrument, surgical tool, surgical implant device, etc.

The camera tracking system 200 includes tracking cameras 204 which may be spaced apart stereo cameras configured with partially overlapping field-of-views. The camera tracking system 200 can have any suitable configuration of arm(s) 202 to move, orient, and support the tracking cameras 204 in a desired location, and may contain at least one processor operable to track location of an individual marker and pose of an array of markers.

As used herein, the term "pose" refers to the location (e.g., along 3 orthogonal axes) and/or the rotation angle (e.g., about the 3 orthogonal axes) of markers (e.g., DRB) relative to another marker (e.g., surveillance marker) and/or to a defined coordinate system (e.g., camera coordinate system). A pose may therefore be defined based on only the multidimensional location of the markers relative to another marker and/or relative to the defined coordinate system, based on only the multidimensional rotational angles of the markers relative to the other marker and/or to the defined coordinate system, or based on a combination of the multidimensional location and the multidimensional rotational angles. The term "pose" therefore is used to refer to location, rotational angle, or combination thereof.

The tracking cameras 204 may include, e.g., infrared cameras (e.g., bifocal or stereophotogrammetric cameras), operable to identify, for example, active and passive tracking markers for single markers (e.g., surveillance marker) and reference arrays which can be formed on or attached to the patient 210 (e.g., patient reference array, DRB), end effector 112 (e.g., end effector reference array), XR headset(s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the markers in order to identify and determine locations of individual markers and poses of the reference arrays in three-dimensions. For example, active reference arrays may include infrared-emitting markers that are activated by an electrical signal (e.g., infrared light emitting diodes (LEDs)), and passive reference arrays may include retro-reflective markers that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track location of a surveillance marker and poses of reference arrays within the XR camera headset field-of-views (FOVs) 152 and 154, respectively. Accordingly, as illustrated in FIG. 1, the location of the surveillance marker and the poses of reference arrays on various objects can be tracked while in the FOVs 152 and 154 of the XR headsets 150 and/or a FOV 600 of the tracking cameras 204.

FIGS. 1 and 2 illustrate a potential configuration for the placement of the camera tracking system 200 and the surgical robot 100 in an operating room environment. Computer-aided navigated surgery can be provided by the camera tracking system controlling the XR headsets 150 and/or other displays 34, 36, and 110 to display surgical procedure navigation information. The surgical robot 100 is optional during computer-aided navigated surgery.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer. This information can be from local sources (e.g., the surgical robot 100 and/or other medical), remote sources (e.g., patient medical image server), and/or other electronic equipment. The camera tracking system 200 may track markers in 6 degrees-of-freedom (6 DOF) relative to three axes of a 3D coordinate system and rotational angles about each axis. The XR headsets 150 may also operate to track hand poses and gestures to enable gesture-based interactions with "virtual" buttons and interfaces displayed through the XR headsets 150 and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 150 while positioned on wearers' heads. The patient reference array 116 (DRB) is generally rigidly attached to the patient with stable pitch and roll relative to gravity. This local rigid patient reference 116 can serve as a common reference for reference frames relative to other tracked arrays, such as a reference array on the end effector 112, instrument reference array 170, and reference arrays on the XR headsets 150.

During a surgical procedure using surgical navigation, a surveillance marker can be affixed to the patient to provide information on whether the patient reference array 116 has shifted. For example, during a spinal fusion procedure with planned placement of pedicle screw fixation, two small incisions are made over the posterior superior iliac spine bilaterally. The DRB and the surveillance marker are then affixed to the posterior superior iliac spine bilaterally. If the surveillance marker's location changes relative to the patient reference array 116, the camera tracking system 200 may display a meter indicating the amount of movement and/or may display a pop-up warning message to inform the user that the patient reference array may have been bumped. If the patient reference array has indeed been bumped, the registration of the patient reference array to the tracked coordinate system may be invalid and could result in erroneous navigation which is off target.

When present, the surgical robot (also "robot") may be positioned near or next to patient 210. The robot 100 can be positioned at any suitable location near the patient 210 depending on the area of the patient 210 undergoing the surgical procedure. The camera tracking system 200 may be separated from the robot system 100 and positioned at the foot of patient 210. This location allows the tracking camera 200 to have a direct visual line of sight to the surgical area 208. In the configuration shown, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 can comprise a guide tube 114, which is configured to receive and orient a surgical instrument, tool, or implant used to perform a surgical procedure on the patient 210.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. The more general term device can also refer to structure of the end-effector, etc. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axis, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a 6 DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 150 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Reference arrays of markers can be formed on or connected to robot arms 102 and/or 104, the end-effector 112 (e.g., end-effector array 114 in FIG. 2), and/or a surgical instrument (e.g., instrument array 170) to track poses in 6 DOF along 3 orthogonal axes and rotation about the axes. The reference arrays enable each of the marked objects (e.g., the end-effector 112, the patient 210, and the surgical instruments) to be tracked by the tracking camera 200, and the tracked poses can be used to provide navigated guidance during a surgical procedure and/or used to control movement of the surgical robot 100 for guiding the end-effector 112 and/or an instrument manipulated by the end-effector 112.

Referring to FIG. 3 the surgical robot 100 may include a display 110, upper arm 102, lower arm 104, end-effector 112, vertical column 312, casters 314, a table 318, and ring 324 which uses lights to indicate statuses and other information. Cabinet 106 may house electrical components of surgical robot 100 including, but not limited, to a battery, a power distribution module, a platform interface board module, and a computer. The camera tracking system 200 may include a display 36, tracking cameras 204, arm(s) 202, a computer housed in cabinet 330, and other components.

In computer-assisted navigated surgeries, perpendicular 2D scan slices, such as axial, sagittal, and/or coronal views, of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System

FIG. 4 illustrates a block diagram of a surgical system that includes an XR headset 150, a computer platform 400, imaging devices 420, and a surgical robot 100 which are configured to operate according to some embodiments.

The imaging devices 420 may include a C-arm imaging device, an O-arm imaging device, and/or a patient image database. The XR headset 150 provides an improved human interface for performing navigated surgical procedures. The XR headset 150 can be configured to provide functionalities, e.g., via the computer platform 400, that include without limitation any one or more of: identification of hand gesture based commands, display XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit (IMU)) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field-of-view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes the camera tracking system 200 which may be connected to a computer platform 400 for operational processing and which may provide other operational functionality including a navigation controller 404 and/or of an XR headset controller 410. The surgical system may include the surgical robot 100. The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector of the surgical robot 100, where the steering information is displayed through the display device 438 of the XR headset 150 and/or another display device to indicate where the surgical tool and/or the end effector of the surgical robot 100 should be moved to perform the surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the I/O-arm imaging device, the patient image database, and/or to other medical equipment through the wired/wireless interface 440.

The surgical system may include a XR headset controller 410 that may at least partially reside in the XR headset 150, the computer platform 400, and/or in another system component connected via wired cables and/or wireless communication links. Various functionality is provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from tracking cameras from the cameras 430 (tracking cameras), signals from the microphone 1620, and/or information from the pose sensor 436 and the gesture sensor 434, to generate information for display as XR images on the display device 438 and/or as other for display on other display devices for user viewing. Thus, the XR headset controller 410 illustrated as a circuit block within the XR headset 150 is to be understood as being operationally connected to other illustrated components of the XR headset 150 but not necessarily residing within a common housing or being otherwise transportable by the user. For example, the XR headset controller 410 may reside within the computer platform 400 which, in turn, may reside within the cabinet 330 of the camera tracking system 200, the cabinet 106 of the surgical robot 100, etc.

Camera Tracking System With Neural Network Prediction of Device Feature Coordinate Locations:

Some embodiments are directed to various camera tracking systems which are configured to directly track a tip of an instrument or other feature of a device using navigation cameras for verification, calibration, and/or navigation during surgery. Although various embodiments are described in the context of tracking an instrument tip, they are not limited thereto and can be used to track any visually recognizable feature of a real device which is modeled in a computer model (e.g., computer aided drawing) of the real device. The real device may correspond to an instrument, end effector, or other apparatus.

Figure 6:
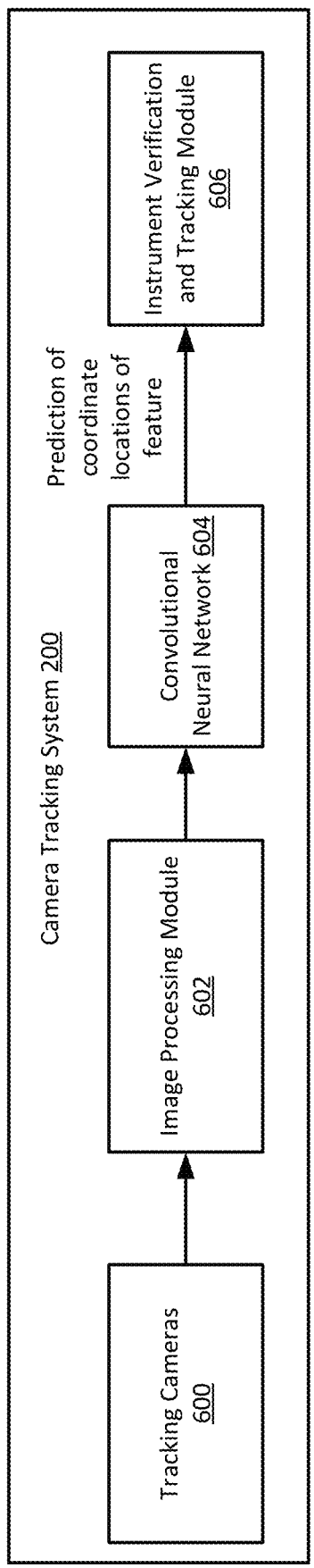
FIG. 6 illustrates components of a camera tracking system which include a neural network to predict coordinate locations of a device feature in images from tracking cameras according to some embodiments.

FIG. 6 illustrates components of a camera tracking system which include a neural network configured to predict coordinate locations of a device feature in images from tracking cameras according to some embodiments. Referring to FIG. 6, the camera tracking system 200 includes tracking cameras 600 such as the cameras 204 in FIG. 1, an image processing module 602, a neural network 604 such as a convolutional neural network, and an instrument verification and tracking module 606.

In accordance with some embodiments, the image processing module 602 identifies locations of markers of a reference array in a set of the images obtained from the tracking cameras 600 imaging a real device with at least partially overlapping field-of-views. The image processing module 602 determines measured coordinate locations of a feature of a real device in the set of the images based on the identified locations of the markers and based on a relative location relationship between the markers and the feature. The system 200 processes a region of interest in the set of the images identified based on the measured coordinate locations through the neural network 604 which is configured to output a prediction of coordinate locations of the feature in the set of the images. The neural network 604 has been trained based on training images containing the feature of a computer model rendered at known coordinate locations. The instrument verification and tracking module 606 tracks pose of the feature of the real device in three-dimensional (3D) space based on the prediction of coordinate locations of the feature of the real device in the set of the images.

In a further embodiment, the prediction of coordinate locations of the feature of the real device, based on output of the neural network 604, indicates predicted pixel coordinates of the feature within the set of the images.

In a further embodiment, the instrument verification and tracking module 606 determines a predicted 3D pose of the feature of the real device in a tracked space based on triangulation of the prediction of two-dimensional (2D) coordinate locations of the feature of the real device in a pair of the set of the images from a pair of the tracking cameras 600. The instrument verification and tracking module 606 determines a measured 3D pose of the feature of the real device in the tracked spaced based on triangulation of the locations of the markers of the reference array in the pair of the set of the images, and calibrates a feature offset based on comparison of the predicted 3D pose of the feature and the measured 3D pose of the feature.

In order to track the real feature(s), also called datum(s), of the real device datums, the computer model (e.g., known CAD data) can be used to train the neural network 604 to return the image pixel coordinates of the feature (datum) requested. In an example scenario, the high contrast optical markers can have tracked locations in the same image frame as an instrument tip to allow operations to calibrate the markers and instrument tip into the same rigid body. In this way, the need for mechanical "verification divots" is eliminated and real-time and automated measurement of the instrumentation and apparatus can be operationally performed. After finding the tip location in left and right stereo cameras, the 3D location is determined using triangulation of the 2D locations. The markers can be similarly identified in 2D imagery before being triangulated to determine their 3D locations.

In a further embodiment, the instrument verification and tracking module 606 verifies the feature of the real device based on whether the measured coordinate locations of the feature of the real device are within a threshold distance of the prediction of coordinate locations of the feature of the real device.

In a further embodiment, training images, which contain the feature of the computer model rendered at the known coordinate locations in the training images, are processed through the neural network 604 to output predictions of coordinate locations of the feature of the computer model in the training images. The known coordinate locations of the feature in the training images are compared to the predictions of coordinate locations of the feature of the computer model in the training images, and parameters of the neural network 604 are trained based on the comparison.

The neural network 604 may be trained using, for example, tens of thousands or millions of images. An alpha image can be generated with a computer generated representation of the device rendering based on the computer model, and which may be rendered with a transparent background. The alpha image can then be augmented with different synthetic backgrounds to generate the training images for use in training the neural network 604. In one embodiments, the training images are generated to contain the feature of the computer model rendered at the known coordinate locations in the training images with different rendered backgrounds, different rendered lighting conditions, and/or different rendered poses of the feature of the computer model between at least some of the training images.

The operation to train the parameters of the neural network 604 may include to adapt weights and/or firing thresholds assigned to combining nodes of at least one layer of the neural network 604, based on the training images containing the feature of the computer model rendered at the known coordinate locations in the training images.

A convolutional neural network 604 (CNN) can be used which is configured to rule in real-time or near-real-time processing images from the tracking cameras 600. CNNs are also known as Shift Invariant or Space Invariant Artificial Neural Networks (SIANN), based on the shared-weight architecture of the convolution kernels or filters that slide along image input features and provide translation-equivariant responses known as feature maps.

In a CNN, the input is a tensor with a shape: (number of inputs)×(input height)×(input width)×(input channels). After passing through a convolutional layer, the image becomes abstracted to a feature map, also called an activation map, with shape: (number of inputs)×(feature map height)×(feature map width)×(feature map channels). Convolutional layers convolve the input and pass its result to the next layer.

Rather than train one neural network to track a plurality of different types of instruments (which may require an excessively large architecture and be very time consuming), in some embodiments a different neural network is trained and used to predict feature coordinate locations of different types of devices. Effective training can in at least some scenarios require thousands of labeled images used for supervised training operations. Training hundreds of relatively small device-type-dedicated neural networks to correspond to hundreds of different types of instruments and other apparatus may be extremely time consuming to the point of being impractical. Accordingly, some embodiments are directed to automating the training, evaluation and deployment via simulator training operations. The simulator can include a photosphere (optionally HORI) with dynamic lighting. The relevant instrument is added into the scene and virtual navigation cameras with very similar lens characteristics capture the reference element and instrument tip in thousands of different poses with widely varying backgrounds. The output images are then processed at the time of training in order to match the navigation cameras themselves. For example, the images may be made monochrome, a brightness constant is applied, noise may be applied with a blur kernel.

Once several thousand to more than one million simulated images are fully augmented, the neural network is trained using the simulated images. Evaluating performance of the neural network involves testing the neural network against thousands of varying test images that are not in the training dataset (i.e., have not been seen by the neural network before). Depending on the result of comparing predicted measurements versus known ground truth, the neural network is either deployed as being successful (for use in operating rooms in accordance with embodiments herein) or failed and sent back for continued training improvement. The neural network may be fast enough that an ensemble of several to dozens of neural network can be trained and run in the field. If the variance between neural network is excessive, the measurement is rejected. Averaging the ensemble output may also improve accuracy by approximately 10% to 30%.

Figure 7:
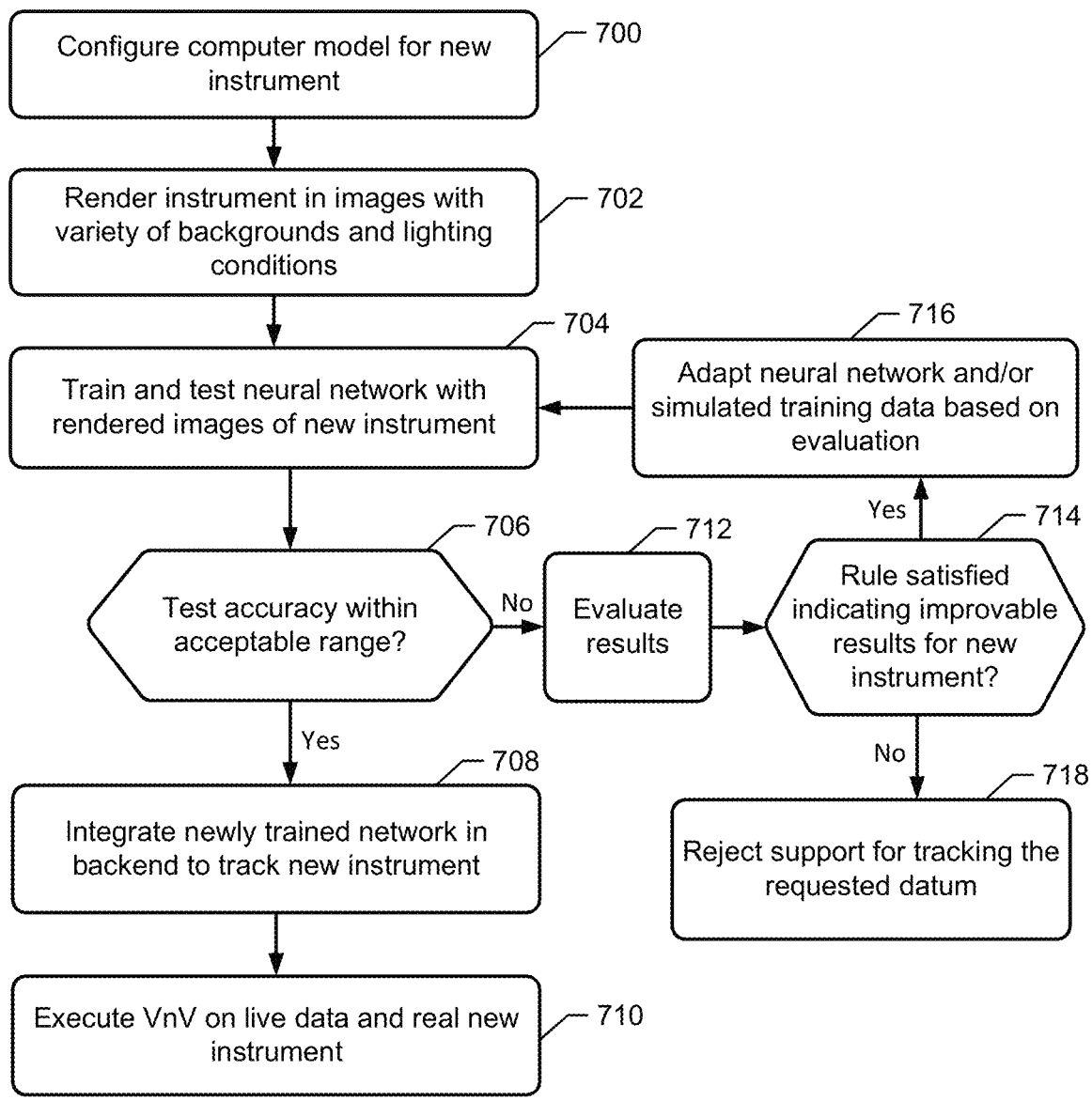
FIG. 7 illustrates a flowchart of operations for identifying, training, testing, and deploying a neural network in an computer automated manner according to some embodiments.

FIG. 7 illustrates a flowchart of operations for identifying, training, testing, and deploying a neural network in an computer automated manner according to some embodiments.

Referring to FIG. 7, a computer model of a new instrument type is configured 700, which may include designing a 3D model of the instrument in a computer-aided design tool. A computer generated image of the tool is rendered 702 in training images with a variety of differing backgrounds and lighting conditions. A neural network is trained (i.e., parameters are trained) and tested 704 using the training images. The testing accuracy is determined 706 and, if the testing accuracy is within an acceptable range, the trained neural network for the new tool type is integrated 708 into a camera tracking system. The neural network can then be executed 710 during a surgical procedure on live image data to verify accuracy of a feature (datum) of the real instrument corresponding to the new instrument type, and to track location of the feature (datum) of the real instrument.

In contrast, when the test accuracy is determined 706 to not be within the acceptable range, the operations evaluate 712 the results and a determination 714 is made whether a rule is satisfied indicating that test accuracy for the new instrument can be improved through further training of the neural network. If the rule is satisfied, operations adapt 716 the neural network and/or the training images data (e.g., varying the backgrounds and lighting conditions) based on the evaluation 712, and the neural network is further trained and tested 704. In contrast, when the rule is not satisfied, the operations indicate 718 rejection of support for tracking the requested feature (datum).

Camera Tracking System With Accuracy Cameras for Device Feature Verification:

In the event that the navigation cameras are not well calibrated or operating room conditions are too uncontrolled and dynamic, other operations can be performed using a specialized verification and calibration fixture attached to visible light optical cameras (also called "accuracy cameras"). The calibration fixture and associated operations can be used an alternative approach to the above-approach of a neural network-based verification of instruments, or may be used in combination with the above-approach.

The operations can use computer vision techniques which are applied to the accuracy cameras working in tandem with existing near-infrared (NIR) tracking cameras 200 (FIG. 2). The computer vision techniques can also make use of neural networks such as any of the embodiments described above.

The operations can provide meaningful visual feedback to the user that includes live feeds of the accuracy cameras video data with diagnostic overlay. When used with an XR headset, the display can present a floating window including either left or right tracking cameras and/or accuracy cameras with a computer-rendered overlay of predicted versus actual computer model, e.g., computer-aided design (CAD), information. Visual guidance to the user can also be shown (e.g., via arrows) directing the user to move the instrument or other device one way or another for improved measurement perspective relative to the accuracy cameras. Similarly, a 3D model can be attached to the end of the instrument or other device for spatial awareness. This information can be to scale or enlarged for enhanced visibility.

Live or paused image or video information can be displayed during or after the verification and/or calibration process on 2D monitor(s). Graphical overlay of measured versus expected information including numbers or other diagnostics can be shown.

In either case, the visualization can update in real time as the instrument and/or other device is moved around, providing intuitive feedback independent of automated measurements. In cases such as incorrect instrument or implant attachments the error may become immediately and intuitively known to surgical staff from these visualizations.

In some embodiments, multiple views of a tracked instrument are captured with the accuracy cameras that are themselves tracked by tracking cameras 200. The instruments and the accuracy cameras include reference elements that are tracked by the tracking cameras 200.

Figure 8:
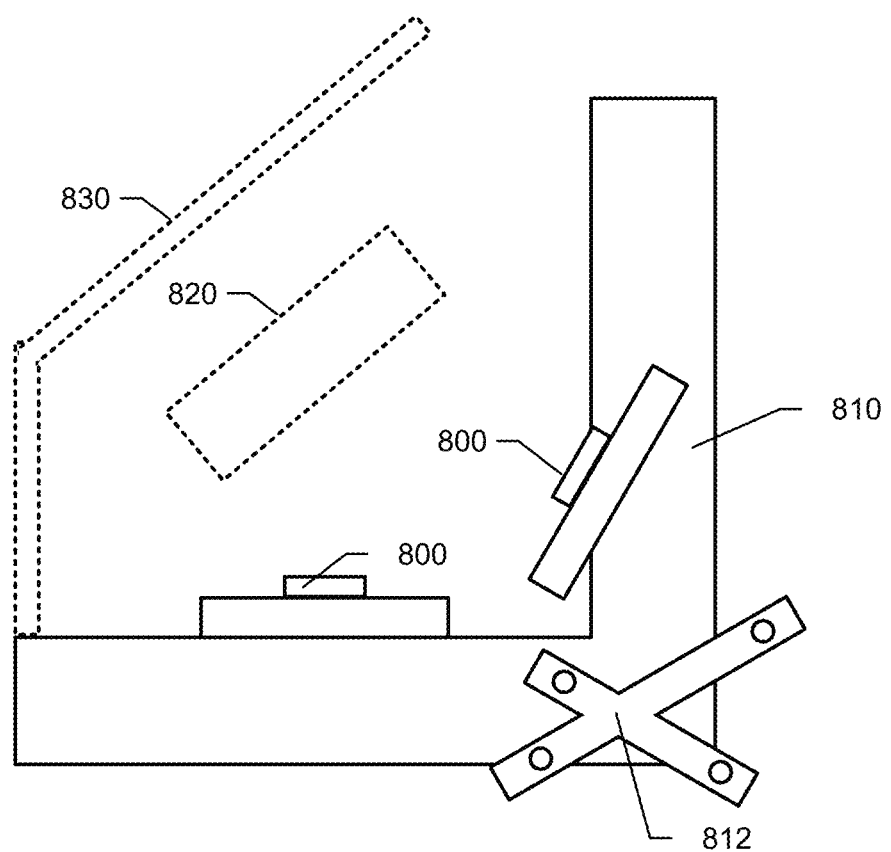
FIG. 8 illustrates a top view of a camera tracking system which includes a pair of accuracy cameras used to verify an instrument or other device for computer assisted navigation during surgery according to some embodiments.

FIG. 8 illustrates a top view of a camera tracking system which includes a pair of accuracy cameras 800 used to verify an instrument or other device for computer assisted navigation during surgery according to some embodiments. The accuracy cameras 800 are connected to a reference array 812 of markers through a rigid fixture 810 to eliminate any movement between the accuracy cameras 800. The accuracy cameras 800 are oriented by the fixture 810 to have at least partially overlapping field-of-views of a verification space 820 in which an instrument feature can be located during verification operations. The accuracy cameras 800 may have higher pixel resolution but have a narrower field-of-view than the tracking cameras 200 since the instrument feature is positioned relatively close in the verification space 820 to the accuracy cameras 800.

A screen 830 may extend from the fixture 810 to be located behind the verification space 820 relative to the accuracy cameras 800. The screen 830 can have a steady or adjustable color and/or provide lighting, e.g., electroluminescent panel, to create a desired background to an instrument being verified while imaged by the accuracy cameras 800. The desired background can improve repeatability, reliability and accuracy of the computer vision techniques when determining 3D location of the instrument feature in images from the accuracy cameras 800.

The accuracy cameras 800 may be covered in a thin sterile transparent drape that is pulled taught (or made from a hard shell) so as to not impact the cameras visibility or add distortion or refraction.

Figure 9:
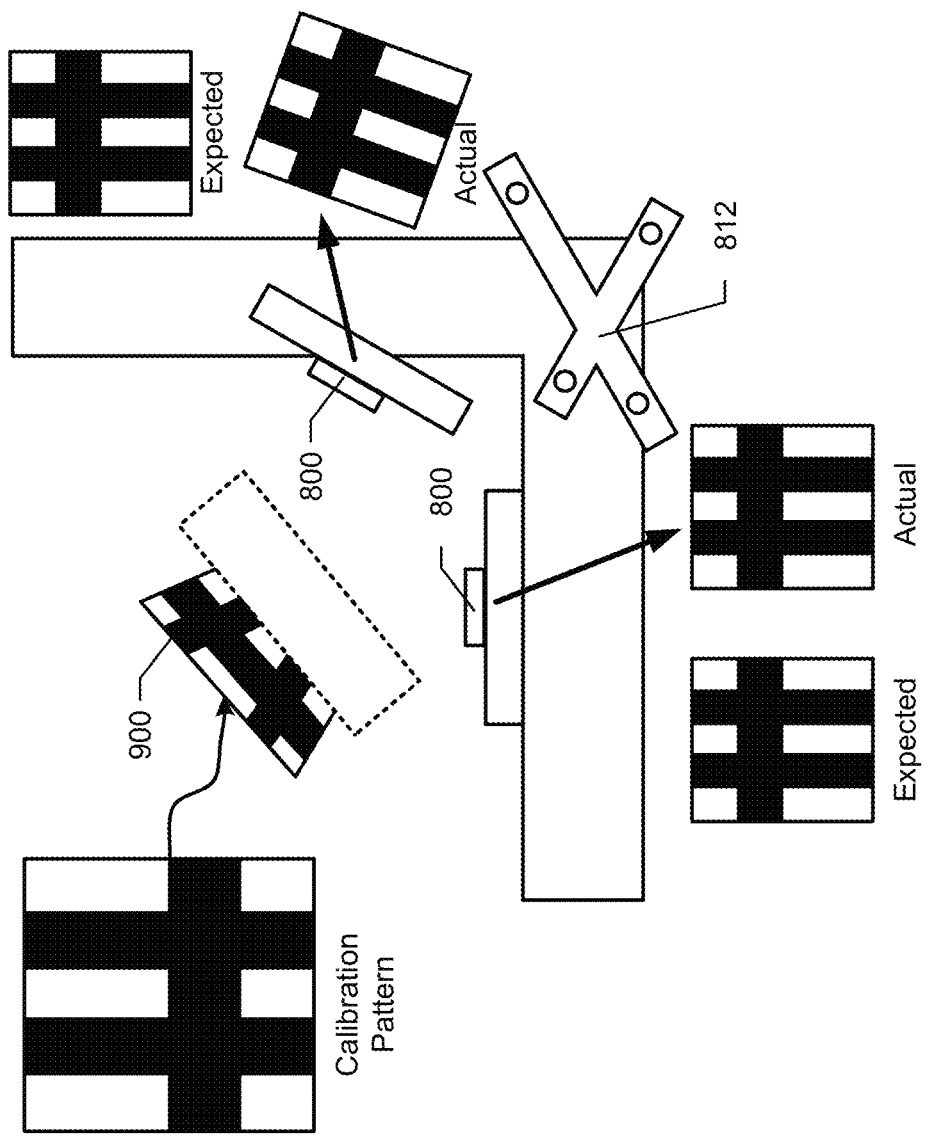
FIG. 9 illustrates another top view of the camera tracking system of FIG. 8 which includes a calibration pattern used to calibrate relative pose of the accuracy cameras according to some embodiments.

A calibration pattern may be used to calibrate the relative pose between the accuracy cameras 800. FIG. 9 illustrates another top view of the camera tracking system of FIG. 8 which includes a calibration pattern 900 that can be used to calibrate relative pose of the accuracy cameras 800 according to some embodiments. The calibration pattern 900 is displayed in the verification space 820 so it is contained in images obtained from the accuracy cameras 800. Operations identify the actual calibration pattern in images from accuracy cameras 800, and compute an expected calibration pattern in images from accuracy cameras 800 based on a relative pose of the accuracy cameras 800. Operations then adjust the relative pose of the accuracy cameras 800 based on difference between the actual calibration pattern and the expected calibration pattern in the images from the accuracy cameras 800. The adjustment of the relative pose may include adjusting a predefined relationship characterizing the distance and angular offset between the accuracy cameras 800.

Figure 10:
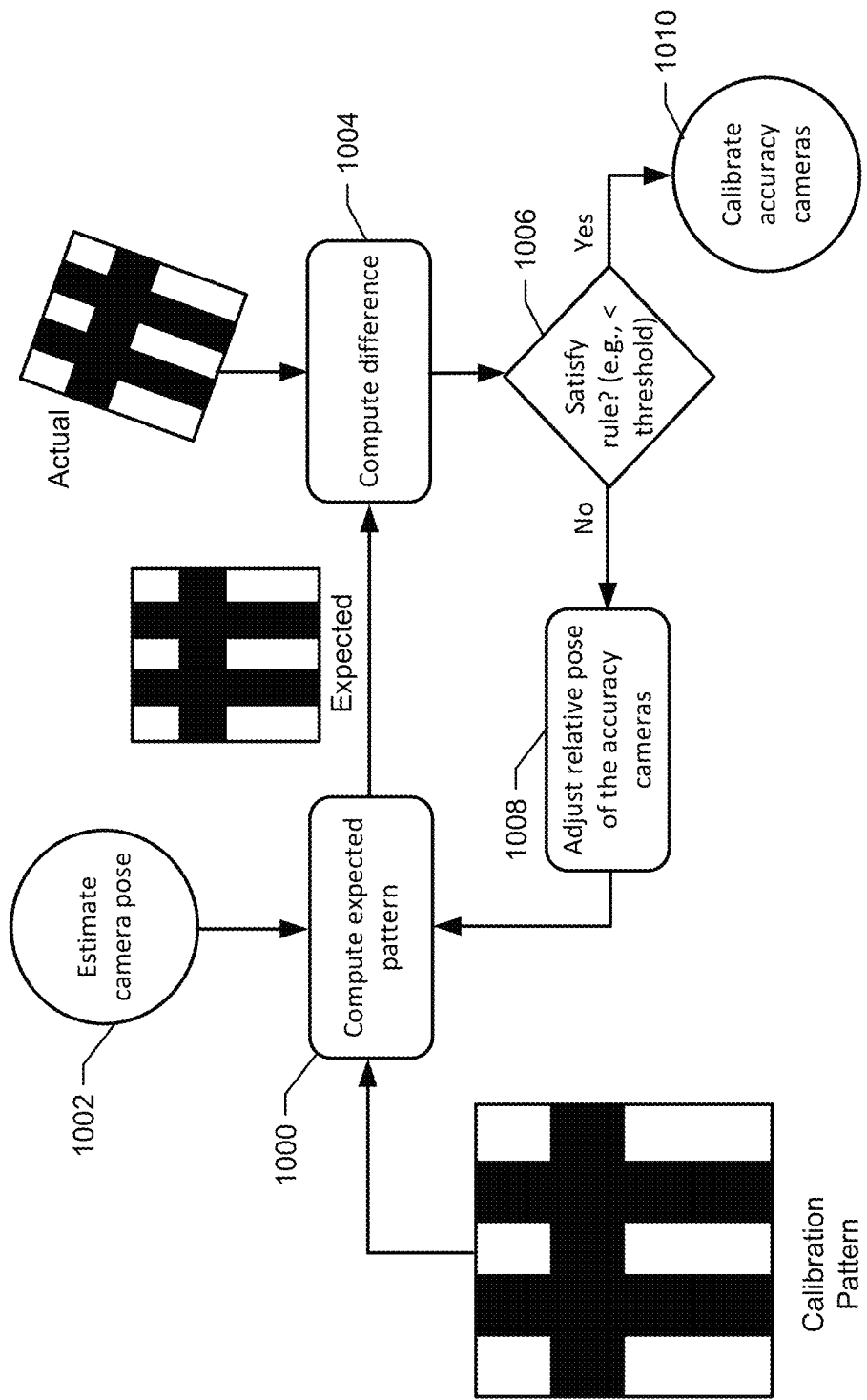
FIG. 10 illustrates a flowchart of operations that may be performed by the camera tracking system of FIG. 8 to calibrate positioning of the accuracy cameras according to some embodiments.

FIG. 10 illustrates a flowchart of operations that may be performed by the camera tracking system of FIG. 8 to calibrate positioning of the accuracy cameras 800 according to some embodiments.

Referring to FIG. 10, the operations estimate 1002 the relative pose (e.g.,) between the accuracy cameras 800, e.g., based on a defined baseline relative pose according to accuracy cameras 800 and the fixture 810. The operations compute 1000 an expected calibration pattern that is expected to be captured in images from the accuracy cameras 800 based on the defined pattern of the calibration pattern and based on the estimate of the relative pose. Operations compute 1004 a difference between the expected calibration pattern and an actual calibration pattern identified in the images from the accuracy cameras 800. When the difference is determined 1006 to satisfy a defined rule, such as by being less than a threshold error, the relative pose between the accuracy cameras 800 is calibrated 1010 based on the then-existing estimate. In contrast, when the difference is determined 1006 to not satisfy the defined rule, the estimate of the relative pose is adjusted 1008 and operations are repeated to compute 1000 another expected pattern, compute 1004 the difference, and to determine 1006 whether the difference satisfies the defined rule.

Figure 11:
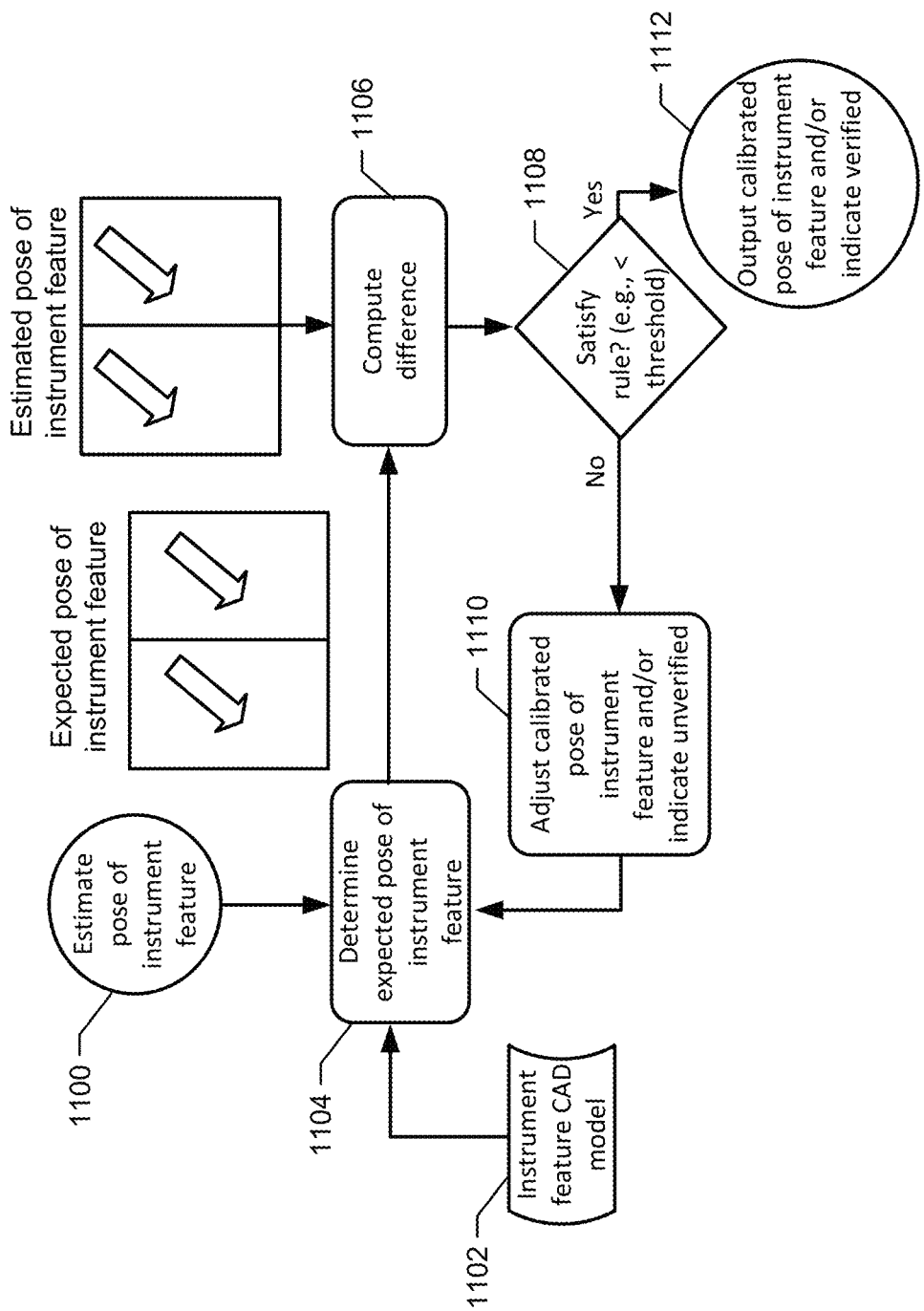
FIG. 11 illustrates a flowchart of operations that may be performed by the camera tracking system of FIG. 8 for computer assisted navigation during surgery according to some embodiments.

FIG. 11 illustrates a flowchart of operations that may be performed by the camera tracking system of FIG. 8 for computer assisted navigation during surgery according to some embodiments.

Referring to FIG. 11, the operations estimate 1100 pose of a feature, e.g., tip, of an instrument based on coordinate locations of the feature identified in a set of images obtained from the accuracy cameras. The operations determine 1104 an expected pose of the instrument feature. The determination 1104 can include to measure pose of markers of a reference array attached to the instrument in a set of images obtained from tracking cameras imaging the reference array and the instrument with at least partially overlapping field-of-views. The determination 1104 further includes to determine expected pose of the feature of the instrument based on a computer model 1102 of the instrument and feature, and the measured pose of the markers of the reference array. In some embodiments, the determination 1104 of the expected pose of the instrument feature may be performed using a neural network to estimate location of the instrument feature in the images from the accuracy cameras 800 and which can be translated to a 3D pose using similar operations to those described for one or more of the embodiments above.

The operations adjust a calibrated pose of the feature of the instrument based on difference between the estimated pose and the expected pose of the feature of the instrument. The adjustment operation can include to compute 1106 a difference between the the estimated pose and the expected pose of the instrument feature. When the difference does not satisfy a defined rule (e.g., feature verification rule), such as by being less than a threshold error, the calibrated pose of the instrument feature can be adjusted 1110 and/or an indication that the instrument feature is unverified can be generated (e.g., displayed to a user), and operations are repeated to determine 1104 an expected pose of the instrument feature, compute 1106 the difference, and to determine 1108 whether the difference satisfies the defined rule. When the difference is determined 1108 to satisfy the defined rule, the calibrated pose of the instrument feature can be output 1112 for use in tracking pose of the instrument feature using the tracking cameras and/or an indication that the instrument feature is verified can be generated (e.g., displayed to a user). When determined 1108 to satisfy the defined rule, the operations can allow tracking of pose of the instrument feature based on pose of the markers of the reference array attached to the instrument in images obtained from the tracking cameras and based on the calibrated pose of the instrument feature.

Figure 5:
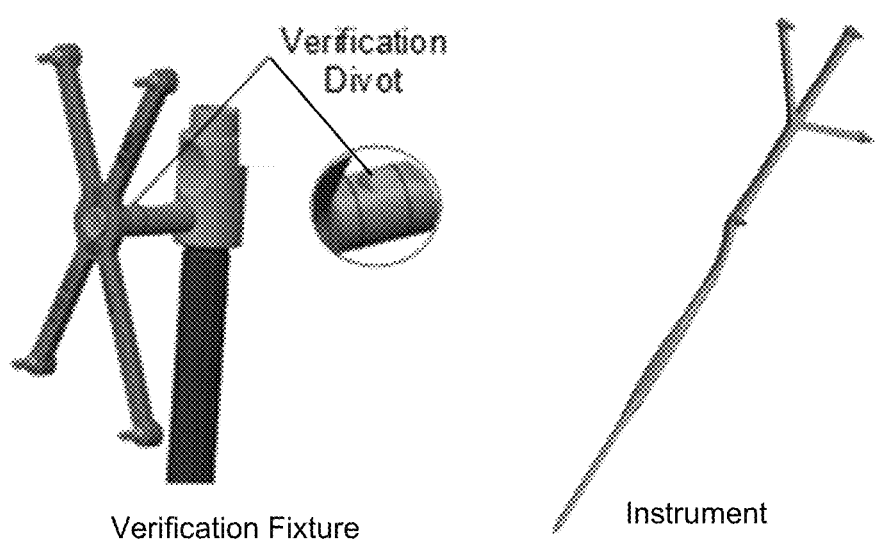
FIG. 5 illustrates an instrument that can be tracked by the camera tracking system as its tip is touched to a verification divot on an arm supporting a tracked reference array which is also tracked by the camera tracking system.

In one specific implementation of FIG. 11, a system for calibrating s surgical device includes a tracking cameras system 200 having a plurality of tracking cameras 204 for tracking navigated surgical devices, a calibration fixture 810 having reference array markers 218 attached thereto and accuracy cameras 800 arranged orthogonally to each other to have at least partially overlapping field-of-views and configured to obtain images of a surgical device (see FIG. 5, for example) having reference array markers such as shown as element 170 in FIG. 1, and a processor for performing the surgical device calibration.

A surgical device needing calibration is placed in the calibration fixture 810. The processor then images the surgical device and performs the following operations.

It estimates pose (e.g., 3D position and orientation) of a physical feature (such as a tip) of the surgical device based on coordinate locations of the feature identified in the set of images obtained from the accuracy cameras 800 and determine pose of the calibration fixture 810 relative to the tracking cameras 204 based on the calibration fixture reference array markers 812 seen by the tracking cameras. Based on the above operations, the processor determines the pose of the physical feature of the surgical device relative to the tracking cameras.

The process further determine expected pose of the surgical device feature based on a computer model of the surgical device and the measured pose of the reference array markers of the surgical device contained in a set of images obtained from the tracking cameras 204. The processor then adjusts pose of the surgical device feature in the computer model based on a difference between the estimated pose and the expected pose of the surgical device feature.

The focal length of the accuracy cameras which need to track just the surgical device being calibrated is typically very small (e.g., in the 10 cm to 60 cm range) relative to the large focal length (e.g., greater than 100 cm) of the tracking cameras which are used to track all navigated tools and instruments in an operating room.

Optical Tracking of Reference Marker Using Negative Spaces (Exposed Contrasting Recessed Surfaces):

Surgical navigation using reference markers that are tracked by tracking cameras has become a desired technique in the operating room. The reference elements are identified using unique geometry patterns created by optical markers. Active optical markers typically emit infrared light in response to a trigger emitted by an optical camera. Passive optical markers glow bright in the spectrum band of interest, typically infra-red, while the rest of the scene is relatively dark.

Figure 12:
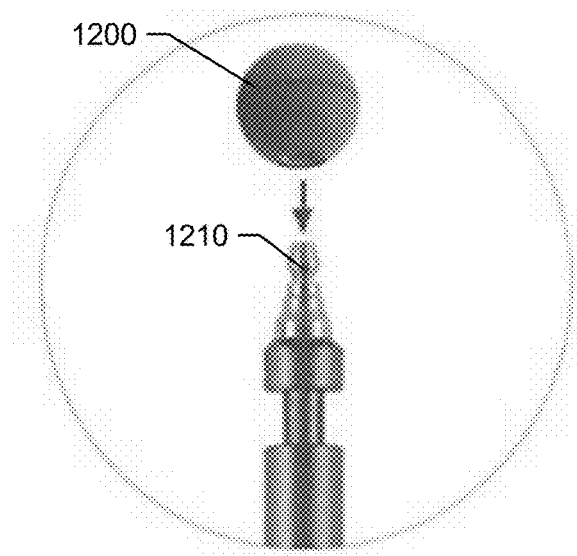
FIG. 12 illustrates a reference marker being attached to a post of an instrument or other device according to some embodiments.

Two technologies for passive markers include spheres and circular disks. A spherical marker can be mounted on a post which allows wide-angle tracking due to the spherical shape and which can be relatively simple to assemble. FIG. 12 illustrates a spherical marker 1200 (reference marker) being attached to a post 1210 of an instrument or other device according to some embodiments. The marker 1200 can include a socket extended into the marker 1200 and adapted to releasably connect the a post 1210 of the instrument, other device, or reference frame. However, a spherical marker can be prone to manufacturing defects that create an imperfect sphere, have high disposable costs since they are not reusable between surgeries, and can become compromised in performance if foreign material occludes a reflective surface of the spherical marker from being imaged. In contrast, a circular disk marker can be mounted in a socket. A circular disk marker can be easier to manufacture than a spherical marker, but still have disposable costs and have a more limited angle of view compared to a spherical marker, and can become compromised in performance if foreign material occludes a reflective surface of the circular disk marker from being imaged.

Reusable optical markers can have a reflective surface which is protected by a protective lens covering that allows it to be wiped down intraoperatively in order to clean off debris.

Various further embodiments of the present disclosure are directed to a reference marker which is configured to be tracked by a camera tracking system for computer assisted navigation during surgery. The reference marker includes an object (e.g., spherical marker or disk marker) with a surface of one of a light absorptive material and a light reflective material, and a cover layer that extends across the surface of the object. The cover layer is the other one of the light absorptive material and the light reflective material. The cover layer has a pattern of openings exposing spaced-apart areas of the surface of the object. The openings can be formed as cut-outs through the cover layer and can have any shape. The exposed spaced-apart areas of the surface of the underlying object form negative spaces that can be tracked using the tracking cameras.

FIGS. 13, 14a, 14b, 15a, 15b, and 16 illustrate a portion of different embodiments of reference markers having a cover layer with a pattern of openings exposing spaced-apart areas of an underlying object surface for tracking by a camera tracking system.

Figure 13:
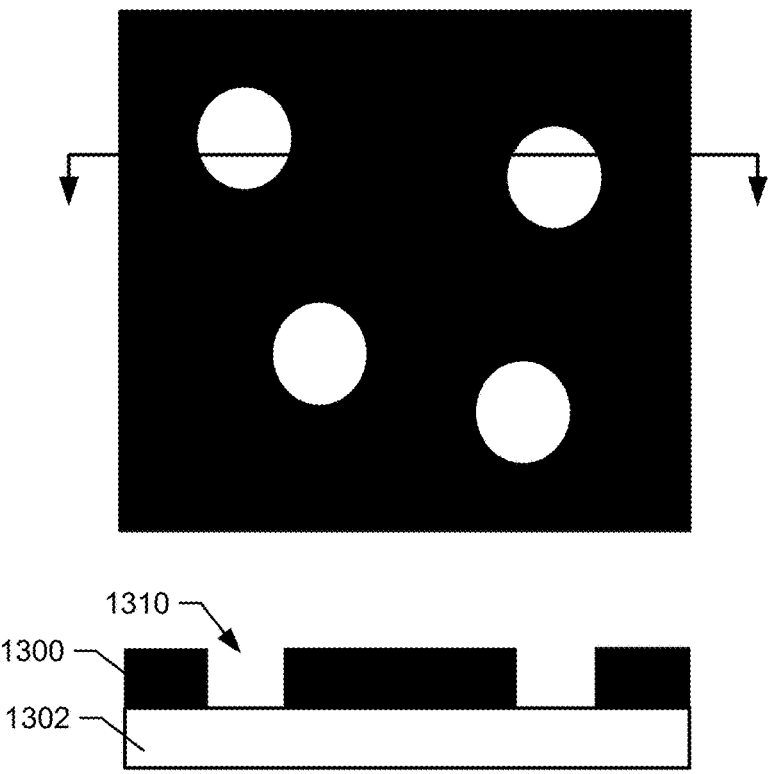

Referring initially to FIG. 13, a top view and a corresponding side-cross-sectional view show the cover layer 1300 with a pattern of openings 1310 exposing spaced-apart areas of an underlying object 1302. The object 1302 may be a sphere and the cover layer 1300 can extend across the surface of the sphere. Alternatively, the object 1302 may be a circular disk and the cover layer 1300 can extend across the surface of the circular disk.

In the embodiment illustrated in FIG. 13, the surface of the object 1302 is a light reflective material, such as anodized aluminum. To provide optical contrast, the cover layer is then a light absorptive material, such as a black-anodized material. In another embodiment, the surface of the object 1302 is a light absorptive material and the cover layer is a light reflective material. An example thickness of the cover layer 1300 can be 200 microns, although the cover layer 1300 may be any thickness such as to provide sufficient depth to obscure one of the spaced-apart areas from being imaged by one or more of the tracking cameras when viewed sufficiently off-camera-axis.

The spaced-apart areas of the surface of the object 1302 exposed through the openings 1302 in the cover layer 1300 are circular shape in some embodiments. In other embodiments the spaced-apart areas can have any other shape, including oval, square, rectangle, etc.

The opaque cover layer 1300 may have a sufficient thickness to obscure some of the patterned spaced-apart areas of the surface of the object 1302 (negative spaces) when imaged by the tracking cameras at an off-axis angle relative to the line-of-sight of the cameras (e.g., cameras 204 in FIGS. 1 and 2). Some further embodiments are directed to avoiding obscuration of the patterned spaced-apart areas of the surface of the object 1302 when imaged off-axis angle by forming the openings in the cover layer to have sloping sidewall surfaces.

FIG. 14a is a side cross-sectional view of a portion of another reference marker which includes a cover layer 1400 with a pattern of openings 1410 exposing spaced-apart areas of an underlying object 1402, which is configured in accordance with one embodiment. The object 1402 may be a sphere or circular disk, and the cover layer 1400 can extend across the surface of the sphere or circular disk. In contrast to the openings 1310 in FIG. 13, the openings 1410 in the cover layer 1400 are formed to have sloping sidewall surfaces. The sloping sidewall openings 1410 can enable wider-field-of-view of the pattern spaced-apart areas of the surface of the object 1302 by the tracking cameras without obscuring by the cover layer 1400.

FIG. 14b is a side cross-sectional view of a portion of another reference marker which includes a cover layer 1400 with a pattern of openings 1420, 1422, and 1424 exposing spaced-apart areas of an underlying object 1402, which is configured in accordance with one embodiment. The openings 1420, 1422, and 1424 in the cover layer 1400 are formed to have sloping sidewall surfaces and different viewing angles relative to a line-of-sight of the tracking cameras. The different viewing angles of the openings 1420, 1422, and 1424 can enable much narrower-field-of-view of the pattern spaced-apart areas of the surface of the object 1302 exposed through the openings 1420, 1422, and 1424 by the tracking cameras.

The reference marker does not need to have a flat surface. Instead, the reference marker may have any shape, and may be custom-shaped (e.g., as a sleeve) to conform to an angled or spherical surface of a device, such as an end-effector or tool.

FIG. 15a is a side cross-sectional view of a portion of another reference marker which includes a cover layer 1500 with a pattern of openings 1510, 1512, 1514 exposing spaced-apart areas of an underlying object 1502 having sloped surfaces, which is configured in accordance with one embodiment. FIG. 15b is a side cross-sectional view of a portion of another reference marker which includes a cover layer 1500 with a pattern of openings 1520, 1522, 1524 exposing spaced-apart areas of an underlying object 1502 having sloped surfaces, which is configured in accordance with one embodiment. The object 1502 may be a sphere, circular disk with raised central area, or other shape, and the cover layer 1400 can extend across the surface. The shape of the sloping sidewall openings 1410 affects the field-of-view of the pattern spaced-apart areas of the surface of the object 1302 exposed through the openings 1510, 1512, 1514, 1520, 1522, and 1524 by the tracking cameras without obscuring by the cover layer 1400. For example, the openings 1510, 1512, 1514 have a wider field-of-view than the openings 1520, 1522, 1524.

In order for the pattern of openings to be registered reliably with the underlying surface of the object, it can be important for the cover layer to attach to the same place on the surface. Moreover, the cover layer should not move relative to the underlying object of the reference marker during tracking. The cover layer may be attached to the underlying surface of the object using pins that nest in holes, raised edges that nest in a slot, or kinematic mounts using magnets.

Some related other embodiments are directed to a camera tracking system for computer assisted navigation during surgery for use with reference markers having covers with openings that expose patterns of spaced-apart areas of an underlying object, such as various of the reference markers disclosed herein. The camera tracking system can be configured to operate to identify coordinates of a pattern of spaced-apart light reflective material areas along a continuous surface of a reference marker attached to a real device in images obtained from tracking cameras imaging the reference marker with at least partially overlapping field-of-views. The camera tracking system is further configured to track pose of the reference marker in 3D space based on the identified coordinates of the pattern of spaced-apart light reflective material areas along the continuous surface of the reference marker.

In some embodiments, tracking cameras can be used to calibrate out the small reference element errors introduced due to tolerances in the cover and/or mating mechanisms. Such calibration may operate to decrease the cost of the covers while also improving accuracy for tracking. In such embodiments, the cover may be made of a flexible and disposable black plastic that conforms to the relevant surfaces of the underlying object and, e.g., snaps on tightly using compliant mechanisms in the cover design.

Figure 16:
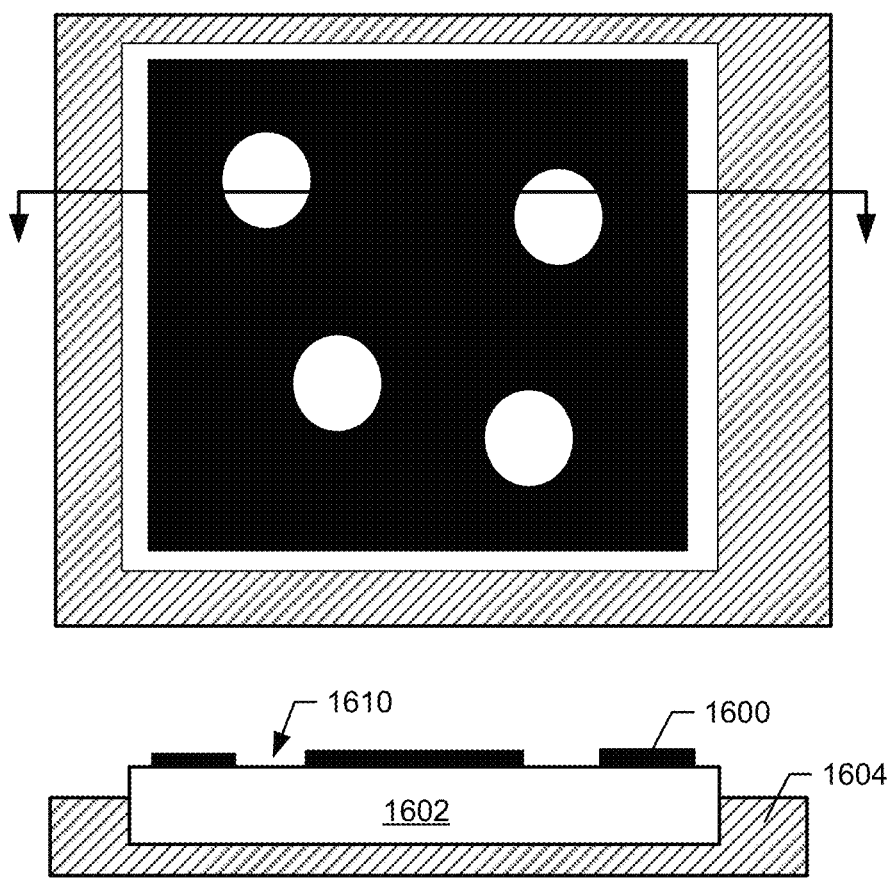

Referring initially to FIG. 16, a top view and a corresponding side-cross-sectional view show a cover layer 1600 with a pattern of openings 1610 exposing spaced-apart areas of an underlying object 1602. The object 1602 may be a sphere and the cover layer 1600 can extend across the surface of the sphere. Alternatively, the object 1602 may be a circular disk and the cover layer 1600 can extend across the surface of the circular disk. The cover layer 1610 may be formed as a thin disposable film or as a reusable hard material, e.g., metal. The relative thinness of the cover layer 1600 avoids the cut-out edges of the openings obscuring view of the exposed areas of a underlying object 1602. When the cover layer 1600 is removable, the cover layer 1600 may attached to defined areas of a a tracking plate 1604 attached or connected to the object 1602, and/or the pattern of openings 1610 can be calibrated using image processing techniques. For example, the rectangular shaped cover layer 1600 can be registered in space relative to the tracking plate 1604, and the pattern of openings 1610 can be registered with respect to the track plate 1604 to allow more accurate tracking of the spaced-apart areas of an underlying object 1602 and, thereby, the reference marker.

In some embodiments, when the surgical robot 100 can be configured to respond to detection of a metallic instrument inserted into the guide-tube 114 by turning off active markers to prevent unwanted motion when an instrument is in contact with the patient. This may make it necessary for the end-effector to be "active", i.e., needing electrical power, driving up design complexity and costs. The end-effector 112 can include cut-outs forming pattern of spaced-apart light reflective material near the guide-tube 114, which can be tracked by tracking cameras. An instrument array can include a cover that will cover the cut-outs when the instrument is inserted in the guide-tube. When the tracking camera cannot detect the end-effector 112 cut-outs near the guide-tube 114, the system can determine that the instrument is in the guide-tube 114 and initiate responsive safety mitigations, such as stopping all motion or allowing only slow motion in a "safe" direction, e.g., away from the patient. In another embodiment, when an instrument inserted in the guide-tube 114 it displaces a cover which exposes cut-outs forming a pattern of spaced-apart light reflective material which was not visible to the camera before insertion of the instrument.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A camera tracking system for computer assisted navigation during surgery, comprising at least one processor operative to:
   identify locations of markers of a reference array in a set of the images obtained from tracking cameras imaging a real device with at least partially overlapping field-of-views;
   determine measured coordinate locations of a feature of a real device in the set of the images based on the identified locations of the markers and based on a relative location relationship between the markers and the feature;
   process a region of interest in the set of the images identified based on the measured coordinate locations through a neural network configured to output a prediction of coordinate locations of the feature in the set of the images, wherein the neural network has been trained based on training images containing the feature of a computer model rendered at known coordinate locations;
   track pose of the feature of the real device in three-dimensional (3D) space based on the prediction of coordinate locations of the feature of the real device in the set of the images;
   determine a predicted 3D pose of the feature of the real device in a tracked space based on triangulation of the prediction of two-dimensional (2D) coordinate locations of the feature of the real device in a pair of the set of the images from a pair of the tracking cameras;
   determine a measured 3D pose of the feature of the real device in the tracked spaced based on triangulation of the locations of the markers of the reference array in the pair of the set of the images; and
   calibrate a feature offset based on comparison of the predicted 3D pose of the feature and the measured 3D pose of the feature.

2. The camera tracking system of claim 1, wherein:
   the prediction of coordinate locations of the feature of the real device indicates predicted pixel coordinates of the feature within the set of the images.

3. The camera tracking system of claim 1, wherein the at least one processor is further operative to:
   verify the feature of the real device based on whether the measured coordinate locations of the feature of the real device are within a threshold distance of the prediction of coordinate locations of the feature of the real device.

4. The camera tracking system of claim 3, wherein the at least one processor is further operative to:
   process training images, which contain the feature of the computer model rendered at the known coordinate locations in the training images, through the neural network to output predictions of coordinate locations of the feature of the computer model in the training images;
   compare the known coordinate locations of the feature in the training images to the predictions of coordinate locations of the feature of the computer model in the training images; and
   train parameters of the neural network based on the comparison.

5. The camera tracking system of claim 4, wherein the at least one processor is further operative to:
   generate the training images containing the feature of the computer model rendered at the known coordinate locations in the training images with different rendered backgrounds, different rendered lighting conditions, and/or different rendered poses of the feature of the computer model between at least some of the training images.

6. The camera tracking system of claim 4, wherein training parameters of the neural network comprises to adapt weights and/or firing thresholds assigned to combining nodes of at least one layer of the neural network, based on the training images containing the feature of the computer model rendered at the known coordinate locations in the training images.

* * * * *